(12) United States Patent
Booker et al.

(10) Patent No.: US 10,034,627 B2
(45) Date of Patent: Jul. 31, 2018

(54) LANCET ASSEMBLY

(71) Applicant: Intrinsyk, LLC, Salem, NH (US)

(72) Inventors: James Keith Booker, Leominster, MA (US); Paul Robert Fuller, Danvers, MA (US); Thomas Ralph Gannon, Litchfield, NH (US)

(73) Assignee: Intrinsyk, LLC, Salem, NH (US)

( * ) Notice: Subject to any disclaimer, the term of this patent is extended or adjusted under 35 U.S.C. 154(b) by 545 days.

(21) Appl. No.: 14/606,061

(22) Filed: Jan. 27, 2015

(65) Prior Publication Data

US 2015/0209068 A1    Jul. 30, 2015

Related U.S. Application Data

(60) Provisional application No. 61/932,365, filed on Jan. 28, 2014.

(51) Int. Cl.
*A61B 5/151* (2006.01)
*A61B 5/15* (2006.01)

(52) U.S. Cl.
CPC ........ *A61B 5/15144* (2013.01); *A61B 5/1513* (2013.01); *A61B 5/150022* (2013.01);
(Continued)

(58) Field of Classification Search
CPC ............ A61B 5/15144; A61B 5/15159; A61B 5/15161; A61B 5/15163; A61B 5/15117;
(Continued)

(56) References Cited

U.S. PATENT DOCUMENTS 5,133,730 A   7/1992  Biro et al.
5,196,025 A * 3/1993  Ranalletta .......... A61B 5/15186
                                                600/583
(Continued)

FOREIGN PATENT DOCUMENTS

CA       105226       2/2005
CA       111499       11/2006
(Continued)

OTHER PUBLICATIONS

International Preliminary Report on Patentability, PCT International Application No. PCT/US2015/012997, dated Aug. 11, 2016.
(Continued)

*Primary Examiner* — Jocelin Tanner
(74) *Attorney, Agent, or Firm* — Kilpatrick Townsend & Stockton LLP

(57) ABSTRACT

Lancet assemblies for puncturing the skin and creating an incision. Upon activation, the disclosed assemblies are configured to move through a firing sequence in which a puncturing instrument extends through an aperture in the device and then is retracted back into a housing of the device and cannot be re-fired. The assemblies are designed so that the aperture in contact with the incision site does not move relative to the incision site during the firing sequence. Accordingly, the tolerance of the assembly is reduced and the reliability of the incisions created by the assembly, including the depth and width of such incisions, is increased.

17 Claims, 14 Drawing Sheets

(52) U.S. Cl.
CPC ...... *A61B 5/15113* (2013.01); *A61B 5/15117* (2013.01); *A61B 5/150259* (2013.01); *A61B 5/150442* (2013.01); *A61B 5/150503* (2013.01); *A61B 5/150908* (2013.01); *A61B 5/150824* (2013.01)

(58) Field of Classification Search
CPC ............ A61B 5/150503; A61B 5/1513; A61B 5/150022; A61B 5/150908; A61B 5/150442; A61B 5/150259; A61B 5/15113; A61B 5/150824
See application file for complete search history.

(56) References Cited

U.S. PATENT DOCUMENTS

| | | | |
|---|---|---|---|
| 5,212,879 A | | 5/1993 | Biro et al. |
| D342,573 S | | 12/1993 | Cerola |
| 5,314,441 A | * | 5/1994 | Cusack ............ A61B 17/32093 606/182 |
| 5,439,473 A | | 8/1995 | Jorgensen |
| 5,527,333 A | | 6/1996 | Nikkels et al. |
| 5,529,581 A | | 6/1996 | Cusack |
| D376,203 S | | 12/1996 | Schraga |
| D376,649 S | | 12/1996 | Kim |
| D379,516 S | | 5/1997 | Rutter |
| 5,628,765 A | | 5/1997 | Morita et al. |
| 5,643,306 A | | 7/1997 | Schraga |
| 5,707,384 A | | 1/1998 | Kim |
| 5,772,677 A | | 6/1998 | Mawhirt et al. |
| 5,797,940 A | * | 8/1998 | Mawhirt .......... A61B 17/32093 606/167 |
| D412,985 S | | 8/1999 | Weekes |
| 6,010,519 A | | 1/2000 | Mawhirt et al. |
| 6,136,013 A | | 10/2000 | Marshall et al. |
| 6,168,606 B1 | | 1/2001 | Levin et al. |
| 6,221,089 B1 | | 4/2001 | Mawhirt |
| 6,248,120 B1 | | 6/2001 | Wyszogrodzki |
| D444,557 S | | 7/2001 | Levaughn et al. |
| 6,258,112 B1 | | 7/2001 | Schraga |
| D447,566 S | | 9/2001 | LeVaughn et al. |
| 6,283,982 B1 | | 9/2001 | LeVaughn et al. |
| D493,536 S | | 7/2004 | Jaeck et al. |
| 6,764,496 B2 | | 7/2004 | Schraga |
| 6,958,072 B2 | | 10/2005 | Schraga |
| D530,424 S | | 10/2006 | Manser et al. |
| D569,975 S | | 5/2008 | Wilkinson et al. |
| 7,704,265 B2 | | 4/2010 | Schraga |
| D616,987 S | | 6/2010 | Brown et al. |
| 7,842,059 B2 | | 11/2010 | Rutynowski |
| D642,264 S | | 7/2011 | Fisher et al. |
| D645,147 S | | 9/2011 | Ruf |
| D645,148 S | | 9/2011 | Ruf |
| 8,052,707 B2 | | 11/2011 | Karbowniczek et al. |
| D651,713 S | | 1/2012 | Shi |
| 8,109,960 B2 | | 2/2012 | Sarna et al. |
| 8,118,825 B2 | | 2/2012 | Schraga |
| 8,142,465 B2 | | 3/2012 | Jankowski et al. |
| 8,454,642 B2 | | 6/2013 | Schraga |
| 8,876,846 B2 | | 11/2014 | Schraga |
| D728,787 S | | 5/2015 | Booker et al. |
| 2002/0077650 A1 | | 6/2002 | Schraga et al. |
| 2003/0050656 A1 | | 3/2003 | Schraga |
| 2003/0199912 A1 | | 10/2003 | Pugh |
| 2005/0288699 A1 | | 12/2005 | Schraga et al. |
| 2007/0095178 A1 | * | 5/2007 | Schraga ............... A61B 5/1411 83/13 |
| 2009/0118754 A1 | | 5/2009 | Wyszogrodzki et al. |
| 2010/0076472 A1 | | 3/2010 | Sun |
| 2010/0168775 A1 | | 7/2010 | Karbowniczek et al. |
| 2010/0168776 A1 | | 7/2010 | Schraga |
| 2010/0318111 A1 | | 12/2010 | Sarna et al. |
| 2011/0144537 A1 | * | 6/2011 | Robbins ........... A61B 5/150022 600/583 |
| 2011/0264131 A1 | | 10/2011 | Sun et al. |

FOREIGN PATENT DOCUMENTS

| | | |
|---|---|---|
| CA | 111503 | 11/2006 |
| CA | 157667 | 4/2015 |
| CA | 158975 | 5/2015 |
| WO | 2008/107382 A1 | 9/2008 |

OTHER PUBLICATIONS

Office Action, Chilean Patent Application No. 2014-002705, dated Feb. 9, 2016, 8 pgs.
International Search Report and Written Opinion, PCT Application No. PCT/US2015/012997, dated Apr. 9, 2015.
Notice of Allowance, Design U.S. Appl. No. 29/487,885, dated Mar. 16, 2015.
http://www.itcmed.com/uploads/literature/tenderfootbrochure, available at least as early as Apr. 13, 2014.
http://www.gbo.com/documents/980132_SkinPunctureManual_108x190_rev01_e, available at least as early as Apr. 13, 2014.
BD Quikheel™ Lancet, The Quikheel Advantage, The Evolution of Heel Sticks, 2002.
NeatNick™, Sweeping Action Heel Lancet, 2013.

* cited by examiner

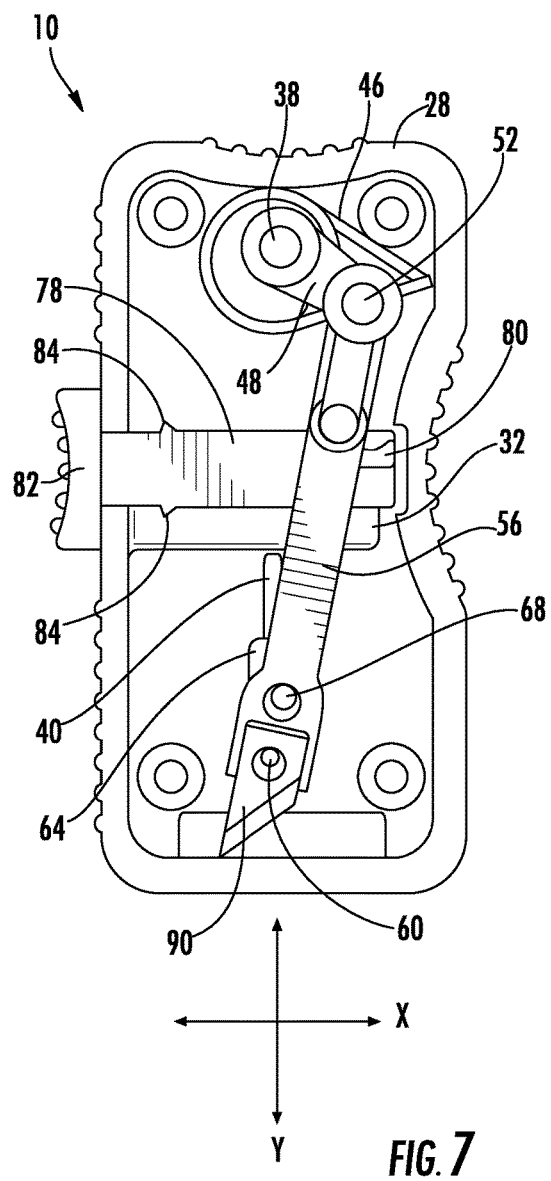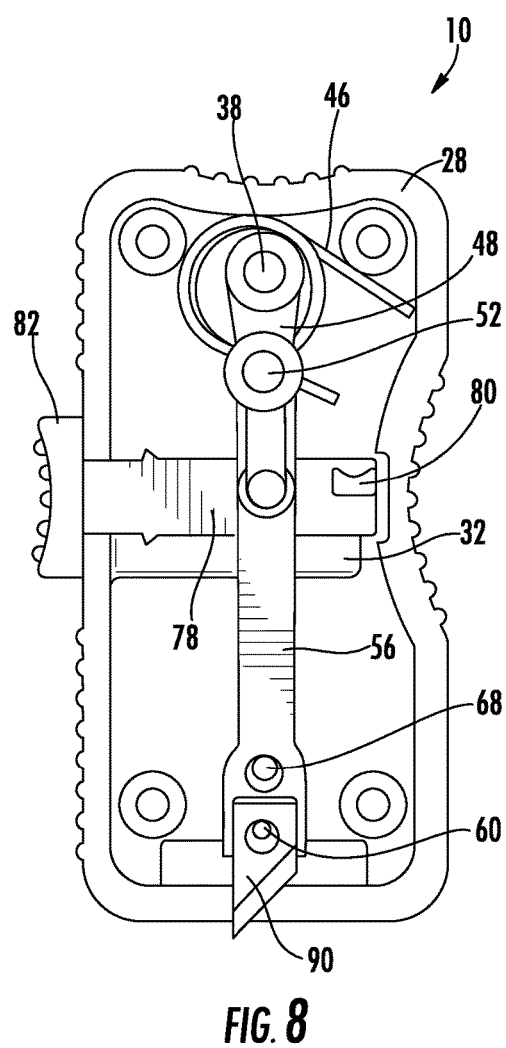
FIG. 7
FIG. 8

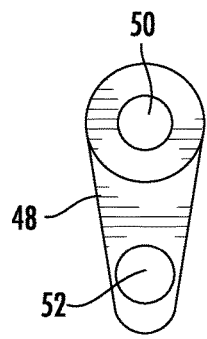
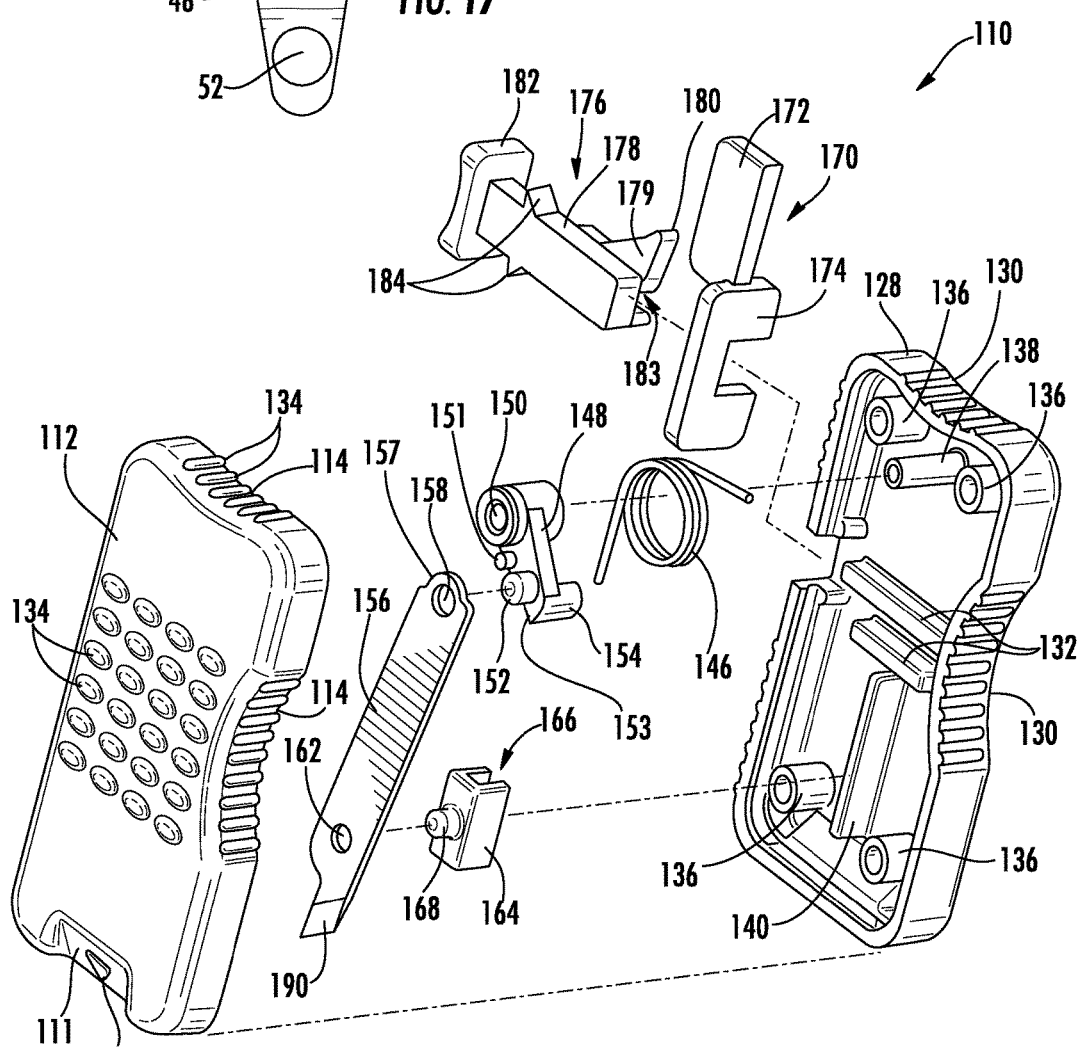

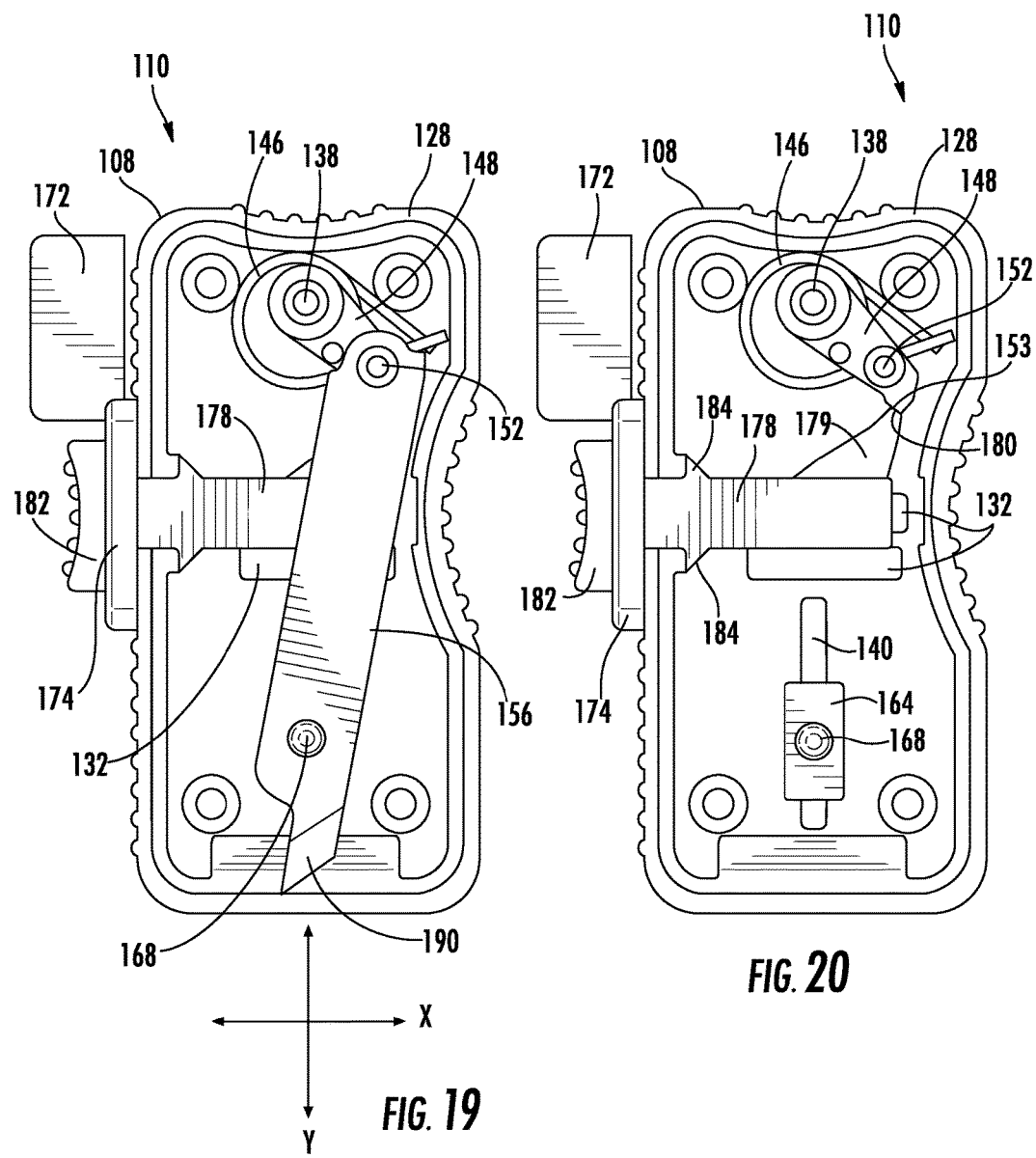

LANCET ASSEMBLY

CROSS REFERENCE TO RELATED APPLICATION

The present application claims the benefit of U.S. Provisional Patent Application No. 61/932,365 filed Jan. 28, 2014 and titled "Lancet Assembly," the content of which is incorporated herein by reference in its entirety.

TECHNICAL FIELD

The present disclosure generally relates to lancet assemblies for creating small incisions in the skin and methods relating to using such lancet assemblies.

BACKGROUND

A lancet is an instrument designed to puncture and make a small incision in the skin to obtain a few drops of blood for testing or otherwise. The puncture can be made on any appropriate area, such as a fingertip. In infants and small children, the incision is usually made in the patient's heel. Typically, the lancet includes a disposable blade that is housed within the device prior to use for safety reasons. Upon activation of the device, the blade is biased by a spring out of the housing and into contact with the user's skin with force sufficient to create the incision. After firing, the blade is retracted back into the housing for safety reasons. To prevent the spread of infectious diseases and otherwise maintain the sterility of the device, such lancets are typically single use devices that cannot be rearmed and re-used once fired.

Many different lancet designs are available. According to one exemplary design, a lancet is positioned against the desired incision site and a portion of the housing is pressed against the incision site, which triggers release of the spring and fires the device. With these types of devices, the lancet housing moves relative to the incision site, which increases the tolerance of the device and leads to more variability in the depth and width of the incision.

SUMMARY

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Disclosed are lancet assemblies for puncturing the skin and creating an incision. Upon activation, the disclosed assemblies are configured to move through a firing sequence in which a blade or other puncturing instrument extends through an aperture in the device and then is retracted back into a housing of the device. After activation, the assemblies are designed so they cannot be reactivated. The assemblies are also designed so that the aperture of the assembly in contact with the incision site does not move relative to the incision site during the firing sequence. Similarly, the housing of the assembly does not move relative to the incision site during the firing sequence. Accordingly, the tolerance of the assembly is reduced and the reliability of the incisions created by the assembly, including the depth and width of such incisions, is increased.

BRIEF DESCRIPTION OF THE DRAWINGS

Illustrative embodiments of the present disclosure are described in detail below with reference to the following drawing figures:

FIG. 7 is a front view of the lancet assembly of FIG. 1, shown in the initial position and with the front cover and the tab removed.

FIG. 8 is a front view of the lancet assembly of FIG. 1, shown in the extended position and with the front cover and the tab removed.

FIG. 17 is a front view of the pivot arm of the lancet assembly of FIG. 1, shown in isolation.

FIG. 18 is a front exploded perspective view of a lancet assembly according to an embodiment.

FIG. 19 is a front view of the lancet assembly of FIG. 18, shown assembled with a tab and in the initial position and with the front cover removed.

FIG. 20 is a front view of the lancet assembly of FIG. 18, shown assembled with a tab, but with the front cover and the blade arm removed.

DETAILED DESCRIPTION

Figure 1:
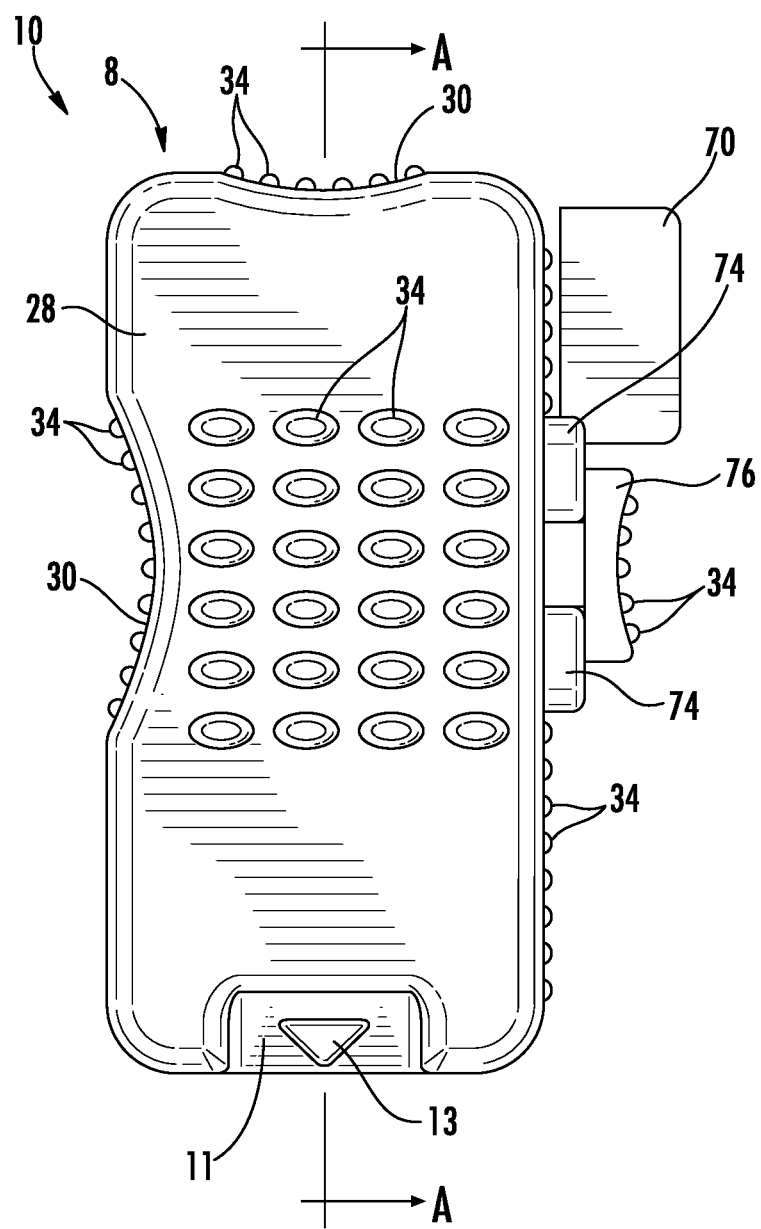
FIG. 1 is a rear view of a lancet assembly according to one embodiment.
Figure 2:
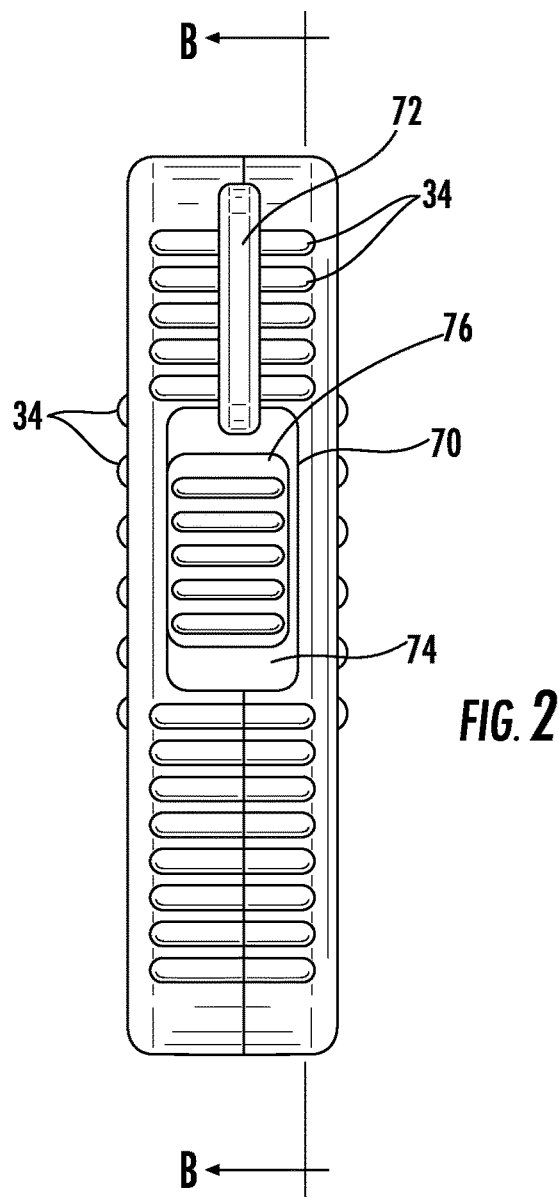
FIG. 2 is a side view of the lancet assembly of FIG. 1.

As shown in the attached Figures, disclosed are lancet assemblies configured to create a small incision in the skin. In particular, the lancet assemblies are designed to create incisions of a certain depth and width (for example, but not limited to, approximately 1.0 mm deep by approximately 2.5 mm wide). The lancet assemblies are designed to move from an initial position (where the puncturing blade is housed within a housing of the assembly and is not externally accessible) to an extended position (where the puncturing blade extends through an aperture of the assembly and exits the housing) to a fired position (where the puncturing blade is housed within the housing of the assembly and cannot be re-fired). As explained in more detail below, the assemblies are easy-to-use and are designed to create incisions having reliable dimensions. In other words, the disclosed assemblies are designed to produce an incision of a given depth and width with less variation in the depth and width of the incision from assembly to assembly than some other devices.

FIGS. 1-16 illustrate lancet assembly 10. Assembly 10 includes a puncturing instrument 90, such as a blade, configured to create a semi-circular slice in the incision site. Assembly 10 includes a housing 8, which as illustrated is a two-piece enclosure made up of a front cover 12 and a rear cover 28. Front cover 12 and rear cover 28 can be snap fit, welded ultrasonically or otherwise, or assembled together in any suitable way. One of front cover 12 and rear cover 28 may include a plurality of posts 20 (positioned on the front cover 12 in the illustrated example) configured to be received within a plurality of corresponding recesses of posts 36 (positioned on the rear cover 28 in the illustrated example) on the other of the front cover 12 and rear cover 28 when the front cover 12 and rear cover 28 are assembled.

The housing optionally includes a plurality of grip features 34. Grip features 34 may be positioned in any desired arrangement along housing 8, such as, but not limited to, along the faces and/or one or more ends of front cover 12 and rear cover 28 and/or along trigger 76. Grip features 34 may be projections, protrusions, ribs, grooves, raised surfaces, or any other suitable features having tactile properties. If desired, housing 8 may have an ergonomic shape. As illustrated in the Figures, front cover 12 may include one or more contours or recesses 14 and rear cover 28 also may include one or more contours or recesses 30 that align with contours or recesses 14 when covers 12, 28 are assembled.

Figure 3:
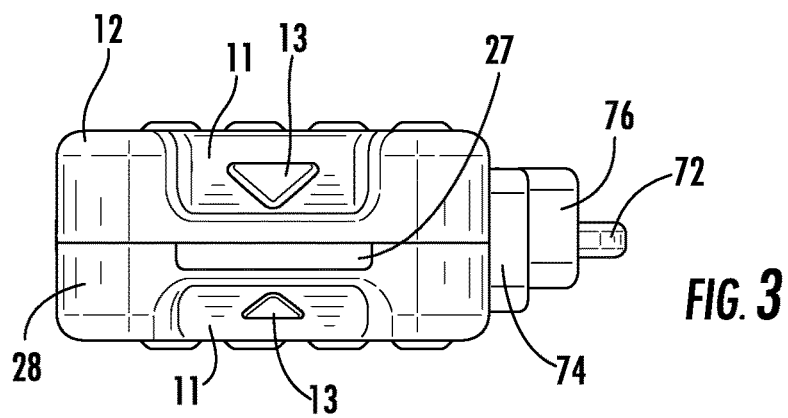
FIG. 3 is a bottom view of the lancet assembly of FIG. 1.

Front cover 12 includes an aperture and rear cover 28 includes an aperture that align to form a slot 27 or other suitable opening when front cover 12 is assembled with rear cover 28. As shown in FIG. 3, slot 27 may be positioned within an end, such as a bottom, of housing 8. When assembly 10 is fired, puncturing instrument 90 extends in a generally Y direction (FIG. 7) through slot 27 and out of housing 8. One or both of front cover 12 and rear cover 28 may optionally include a recessed portion 11 and/or indicia 13 to indicate where the puncturing instrument 90 will exit the assembly 10 upon firing to aid in positioning assembly 10 properly with respect to the intended incision site.

Figure 6:
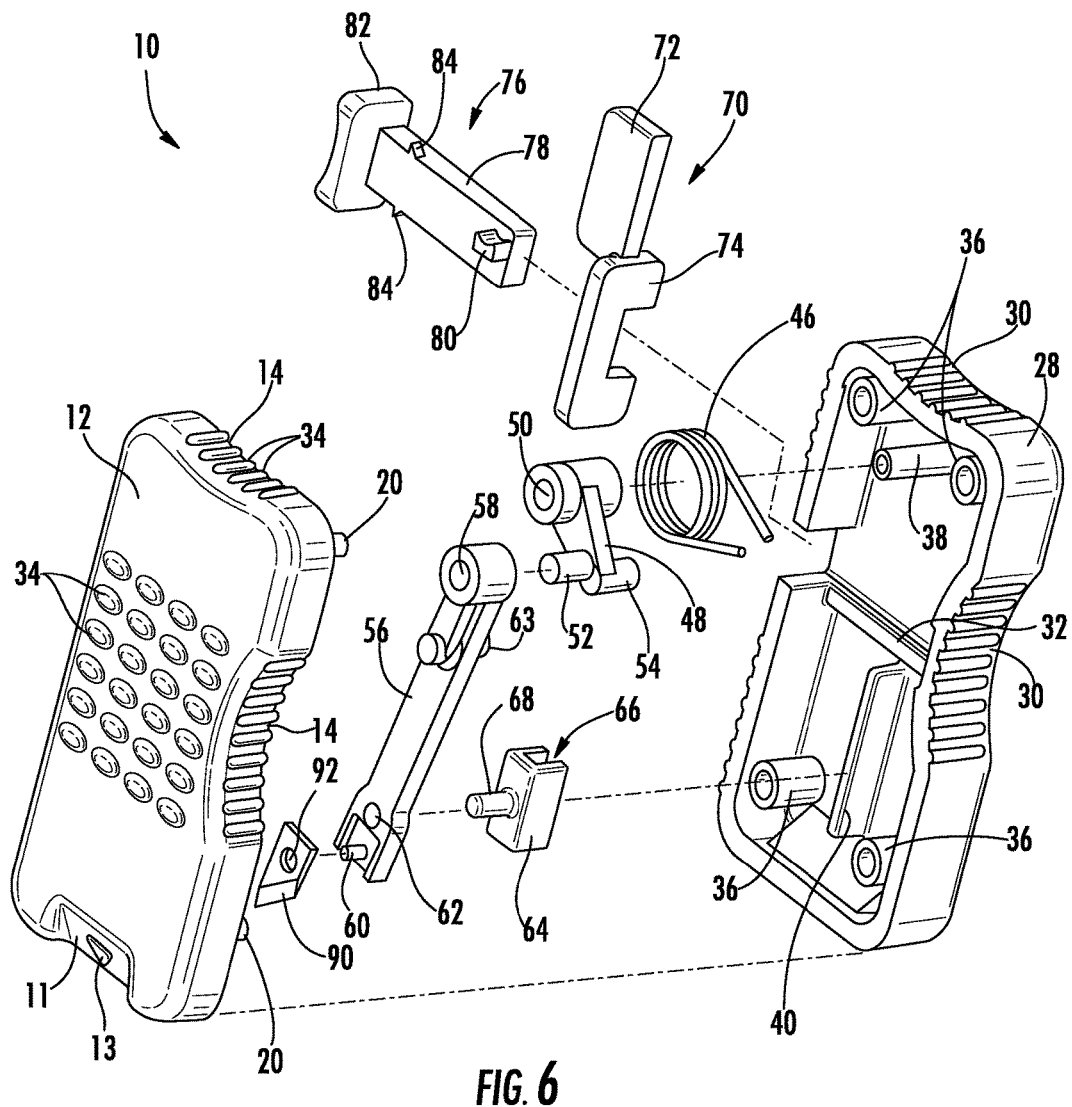
FIG. 6 is a front exploded perspective view of the lancet assembly of FIG. 1.

With reference to FIG. 6, assembly 10 also includes a trigger 76, a spring 46, a slider 64, a pivot arm 48, a blade arm 56, a puncturing instrument 90, and an optional tab 70. Puncturing instrument 90 may be a separate component from blade arm 56 as shown in FIG. 6, or may be integrated with the blade arm, as illustrated in FIGS. 18-30. If puncturing instrument 90 is separate from blade arm 56, puncturing instrument 90 may be coupled with blade arm 56 in any suitable way. As one non-limiting example, recess 92 of puncturing instrument 90 receives a post 60 on blade arm 56. Recess 92 alternatively could be located on the blade arm 56 and the post 60 could be located on puncturing instrument 90. Puncturing instrument 90 may be coupled with or adhered to blade arm 56 in any suitable way, such as by soldering, heat staking, welding, gluing, etc.

Figure 16:
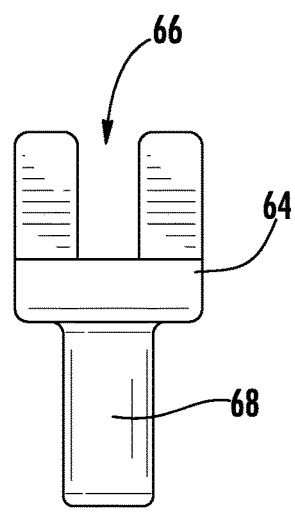
FIG. 16 is a top view of the slider of the lancet assembly of FIG. 1, shown in isolation.

One end of blade arm 56 is coupled with slider 64 and the opposite end of blade arm 56 is coupled with pivot arm 48. As shown in FIGS. 6 and 16, slider 64 includes a channel 66 that slidably cooperates in direction Y (FIG. 7) with a rail 40 disposed on rear cover 28. As illustrated, slider 64 includes a post 68 that is received within a recess 62 of blade arm 56, although slider 64 and blade arm 56 may be coupled in any suitable way. Because blade arm 56 is coupled with slider 64, blade arm 56 will translate in the Y direction along rail 40 as slider 64 translates along rail 40.

Pivot arm 48 interfaces with rear cover 28 in any suitable way to permit pivot arm 48 to rotate about a pivot point. As illustrated, pivot arm 48 includes a recess 50 that receives a post 38 of rear cover 28. In this way, pivot arm 48 is permitted to rotate about post 38. Pivot arm 48 is coupled with blade arm 56 in any suitable way. As one non-limiting example, a post 52 of pivot arm 48 is received within a recess 58 of blade arm 56. Because blade arm 56 is coupled with pivot arm 48, blade arm 56 will rotate about post 38 as pivot arm 48 rotates about post 38. Since blade arm 56 is coupled with both pivot arm 48 and slider 64, blade arm 56 is capable of both rotational and translational movement.

Figures 4, 5:
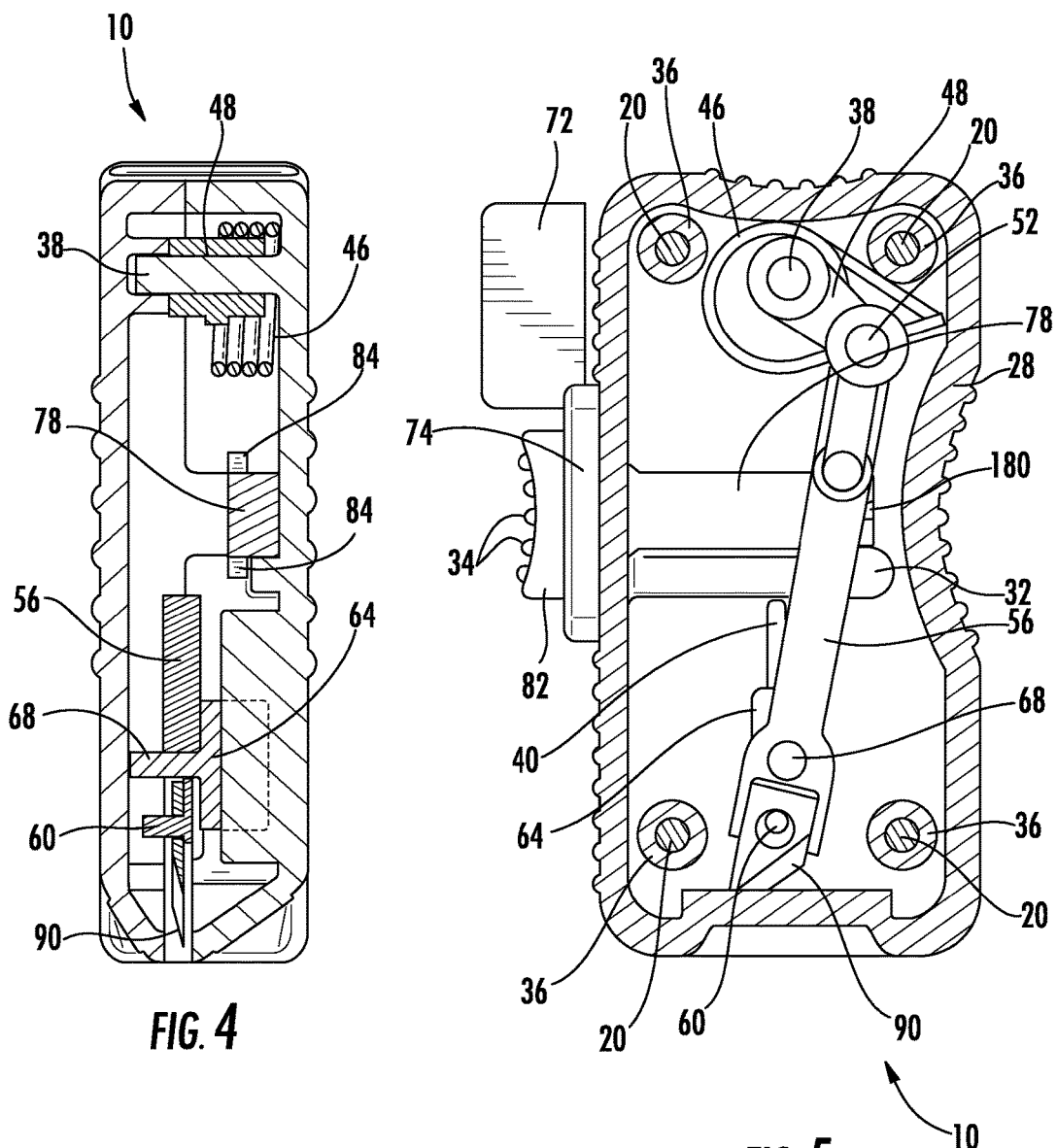
FIG. 4 is a section view of the lancet assembly of FIG. 1, taken along line A-A of FIG. 1 and shown assembled with a tab and in the initial position.
FIG. 5 is a section view of the lancet assembly of FIG. 1, taken along line B-B of FIG. 2 and shown assembled with a tab and in the initial position.
Figures 9, 10:
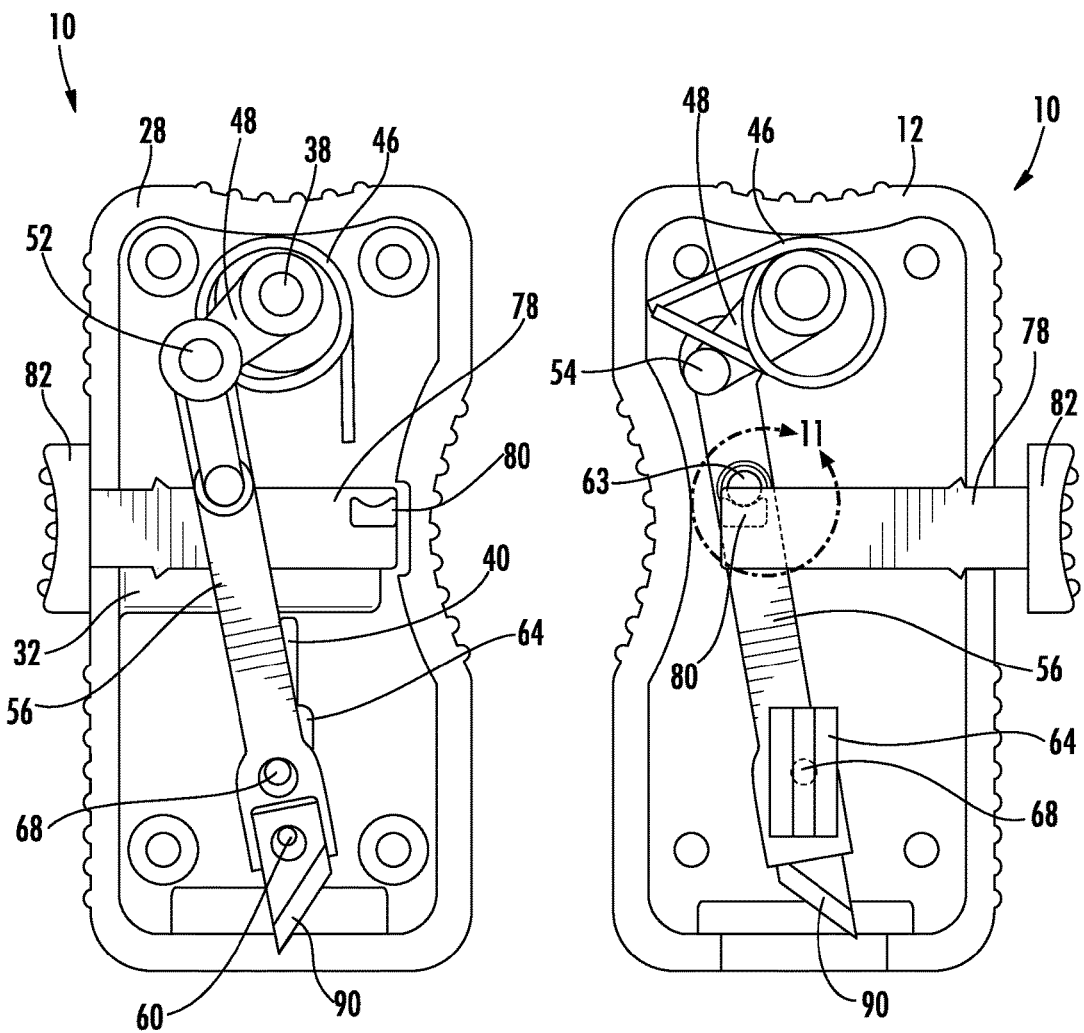
FIG. 9 is a front view of the lancet assembly of FIG. 1, shown in the fired position and with the front cover and the tab removed.
FIG. 10 is a rear view of the lancet assembly of FIG. 1, shown in the initial position and with the rear cover and the tab removed.
Figure 11:
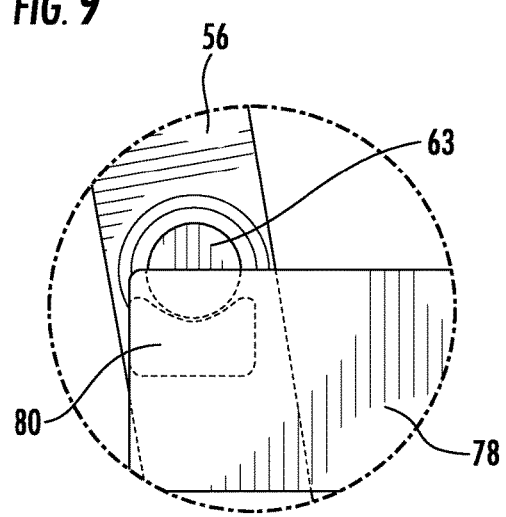
FIG. 11 is an enlarged view of a portion of FIG. 10, taken at inset circle 11.

Pivot arm 48 is disposed within assembly 10 so that it cooperates with spring 46. Spring 46 may be any suitable spring, such as, but not limited to, a torsion, extension, helical, or compression spring, and may be positioned within assembly 10 in any desired way. For example, assembly 10 may be configured so that spring 46 cooperates with blade arm 56 instead of or in addition to pivot arm 48. As illustrated, pivot arm 48 includes a post 54 that engages with spring 46 when assembly 10 is in the initial position. When assembly 10 is in the initial position, as shown in FIGS. 5 and 10-11, spring 46 is deformed. In some cases, the ends of spring 46 are wedged between post 36 of rear cover 28 and post 54 of pivot arm 48, although spring 46 can be arranged in its deformed state in other ways.

Assembly 10 also includes a trigger 76. Trigger 76 has a button 82 and a body 78 that, as shown in FIGS. 7-10, extends into the housing 8 of assembly 10. Body 78 is configured to translate generally in direction X (FIG. 7) along track 32 of rear cover 28. Trigger 76 may also include projections 84, which engage with the edge of cover 12 (FIG. 10) to help keep assembly 10 in the initial position. As shown in FIGS. 10-11, body 78 of trigger 76 includes a detent 80 configured to receive a protrusion 63 or other feature of blade arm 56 when assembly 10 is in the initial position. The engagement between protrusion 63 and detent 80 maintains assembly 10 in the initial position and keeps spring 46 in its deformed state. Optionally, spring 46 is arranged within housing 8 such that its deformation is in more than one plane. The out of plane force generated by spring 46 helps keep the blade arm 56 and slider 64 spring-loaded in the assembly while in the initial position.

Figure 12:
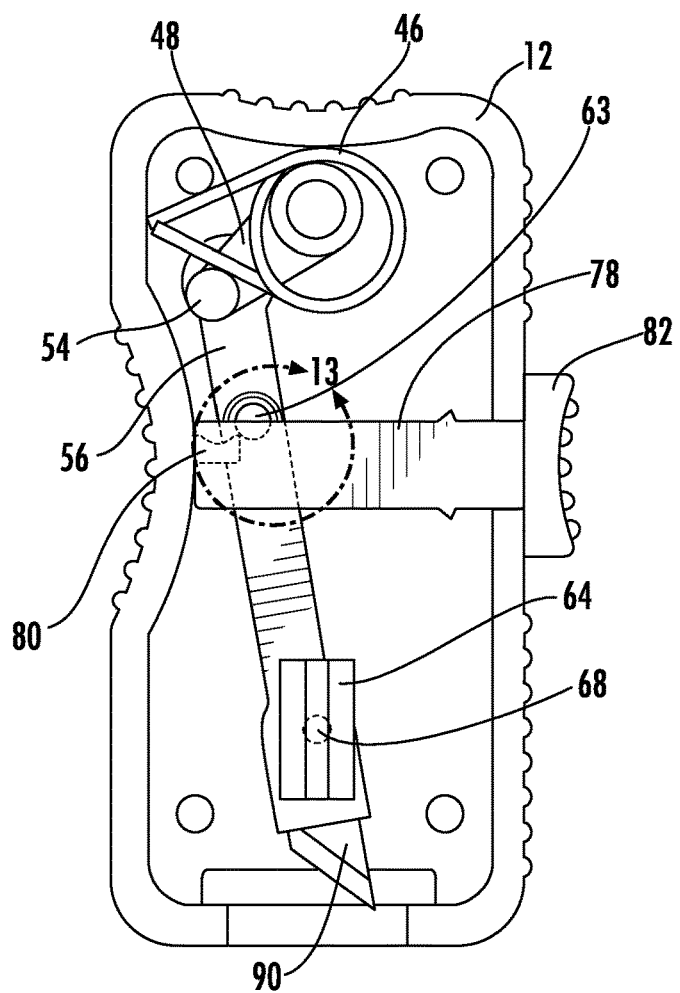
FIG. 12 is a rear view of the lancet assembly of FIG. 1, shown as the assembly moves out of the initial position and with the rear cover and the tab removed.
Figure 13:
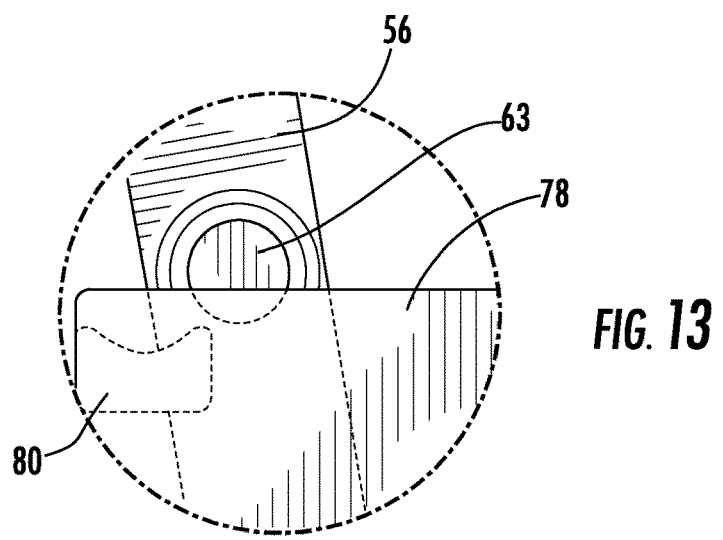
FIG. 13 is an enlarged view of a portion of FIG. 12, taken at inset circle 13.
Figure 15:
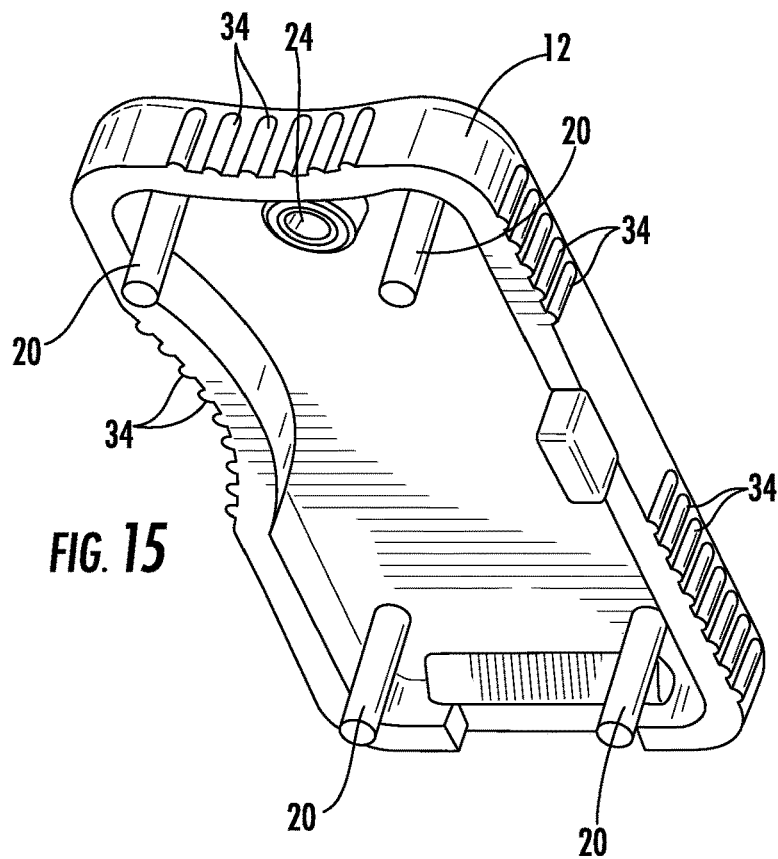
FIG. 15 is a rear perspective view of the front cover of the lancet assembly of FIG. 1, shown in isolation.
Figure 14:
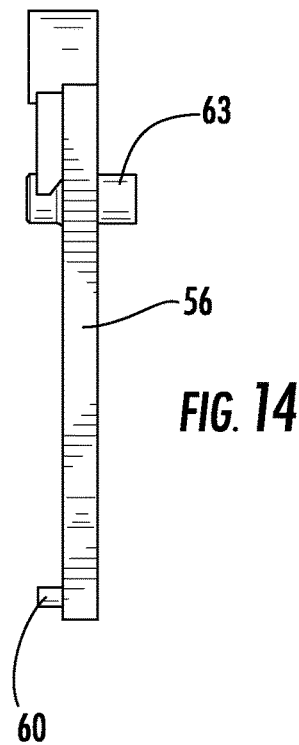
FIG. 14 is a side view of the blade arm of the lancet assembly of FIG. 1, shown in isolation.

To fire assembly 10, button 82 is pushed in the generally X direction to translate trigger body 78 along track 32. As trigger body 78 translates in the generally X direction, detent 80 slides past protrusion 63, as shown in FIGS. 7 and 12-13, thus releasing blade arm 56 relative to trigger 76. Once blade arm 56 is released, the energy stored in spring 46 is released and causes pivot arm 48 to rotate about post 38 until the energy of spring 46 is expended. Track 32 helps keep the trigger body 78 in position and resists the tendency of the pivot arm 48 to pull trigger body 78 down as pivot arm 48 rotates.

Because pivot arm 48 is coupled with blade arm 56, blade arm 56 also rotates about post 38 as pivot arm 48 rotates. As blade arm 56 rotates about post 38, it also translates in the Y direction along rail 40 due to its coupling with slider 64. Specifically, blade arm 56 first translates in the Y direction downward along rail 40 as assembly 10 moves from the initial position to the extended position, thus pushing puncturing instrument 90 out of the housing 8 through slot 27. Next, blade arm 56 translates in the Y direction upwards along rail 40 as assembly 10 moves from the extended position to the fired position, thus retracting puncturing instrument 90 back up into housing 8. FIGS. 7-9 illustrate assembly 10 as it moves away from its initial position to its extended position (FIG. 8) and into its fired position (FIG. 9). Once assembly 10 has been fired, assembly 10 cannot be rearmed and re-fired, as the energy in spring 46 has already been expended.

Assembly 10 optionally may include a tab 70 that cooperates with trigger 76 to prevent premature firing of the assembly 10. Tab 70 includes a gripping portion 72 and an interfacing portion 74. Interfacing portion 74 surrounds button 82 of trigger 76 and prevents body 78 from translating within assembly 10. Once tab 70 is removed, button 82 is free to move in the generally X direction and initiate firing of assembly 10.

Various modifications may be made to assembly 10 while maintaining its operation. As one non-limiting example, trigger 76 may cooperate in numerous ways with blade arm 56, or may instead cooperate with pivot arm 48, to maintain assembly 10 in its initial position. As another non-limiting example, spring 46 may engage with pivot arm 48 or blade arm 56 in any suitable way to urge assembly 10 from its initial position to its extended position and ultimately to its fired position. As yet another non-limiting example, puncturing instrument 90, blade arm 56, slider 64, and pivot arm 48 may be coupled together and cooperate with housing 8 in any suitable way.

FIGS. 18-20 illustrate lancet assembly 110. Like assembly 10, assembly 110 illustrated in FIGS. 18-20 includes a front cover 112 and a rear cover 128 that are assembled together in any suitable manner to form a housing 108. If desired, assembly 110 may include contours or recesses 114 and 130, grip features 134, recesses 111 and/or indicia 113 as explained above.

With reference to FIG. 18, assembly 110 includes a trigger 176, a spring 146, a slider 164, a pivot arm 148, a blade arm 156 with an integrated puncturing instrument 190, and an optional tab 170. As with blade arm 56, one end of blade arm 156 is coupled with slider 164 in any suitable way and the opposite end of blade arm 156 is coupled with pivot arm 148 in any suitable way. Slider 164 includes a channel 166 that slidably cooperates in direction Y (FIG. 19) with a rail 140 disposed in rear cover 128. As illustrated, slider 164 includes a post 168 configured to be received within a recess 162 of blade arm 156, although slider 164 and blade arm 156 may be coupled in any suitable way. Pivot arm 148 interfaces with rear cover 128 in any suitable way to permit pivot arm 148 to rotate about a pivot point. As illustrated, pivot arm 148 includes a recess 150 that receives post 138 of rear cover 128. In this way, pivot arm 148 is capable of rotating about post 138. As illustrated, a post 152 of pivot arm 148 is configured to be received within recess 158 of blade arm 156, although pivot arm 148 and blade arm 156 may be coupled in any suitable way. Because blade arm 156 is coupled with both pivot arm 148 and slider 164, blade arm 156 is capable of both rotational and translational movement, as described in detail above.

Pivot arm 148 is disposed within assembly 110 so that it cooperates with spring 146. Spring 146 may be any suitable spring, such as, but not limited to, a torsion, extension, or compression spring, and may be positioned within assembly 10 in any desired way. Optionally, spring 146 is arranged within housing 108 to cooperate with blade arm 156 in addition to, or instead of, pivot arm 148. As illustrated, pivot arm 148 includes a post 154 that engages spring 146 when assembly 110 is in the initial position. Pivot arm 148 also includes an abutting surface 153, illustrated in FIG. 20 and described below. When assembly 110 is in the initial position, as described above with respect to assembly 10, spring 146 is deformed. In some cases, spring 146 is wedged between post 136 of rear cover 128 and post 154 of pivot arm 148 to maintain it in the deformed state, although spring 146 may be arranged in other ways. In some cases, spring 146 is arranged within housing 108 such that its deformation is in more than one plane. The out of plane force generated by spring 146 helps keep the blade arm 156 and slider 164 spring-loaded in the assembly while in the initial position.

Assembly 110 also includes a trigger 176. Trigger 176 has a button 182 and a body 178 that, as shown in FIGS. 19-20, extends in the X direction into the housing 108 of assembly 110. Body 178 includes a channel 183 configured to translate generally in the direction X along tracks 132 of rear cover 128. Trigger 176 may also include projections 184, which engage with the edge of cover 112 to help maintain assembly 110 in the initial position. As shown in FIGS. 18 and 20, an extension 179 extends upwardly from body 178. Extension 179 includes an abutting surface 180 that, as shown in FIG. 20, abuts abutting surface 153 of pivot arm 148 when assembly 110 is in the initial position. Abutting surfaces 153, 180 may be generally planar or have other corresponding configurations. The engagement between abutting surfaces 180 and 153 maintains assembly 110 in the initial position and keeps spring 146 in its deformed state. Alternatively, abutting surface 180 of trigger 176 may engage with a portion of blade arm 156 to maintain assembly 110 in the initial position.

To fire assembly 110, button 182 is pushed in the generally X direction to translate trigger body 178 along tracks 132. As trigger body 178 translates in the generally X direction, the engagement between abutting surfaces 180 and 153 is released, thus releasing pivot arm 148 relative to trigger 176. Once pivot arm 148 is released, the energy stored in spring 146 is released and causes pivot arm 148 to rotate about post 138, which in turn causes blade arm 156 to pivot and translate as described above. As blade arm 156 moves through its arc of motion, puncturing instrument 190 extends out of the housing 108 in a generally Y direction through a slot and then retracts back into the housing 108 of the assembly in a generally Y direction. Tracks 132 help keep the trigger 176 in position and resist the tendency of the pivot arm 148 to pull trigger 176 down as pivot arm 148 rotates. Once assembly 110 has been fired, assembly 110 cannot be rearmed and re-fired, as the energy in spring 146 has already been expended. Assembly 110 may optionally include a tab 170 that functions similarly to tab 70 described above to prevent assembly 110 from firing prematurely.

As with assembly 10, various modifications may be made to assembly 110 while maintaining its operation. As one non-limiting example, trigger 176 may cooperate in numerous ways with pivot arm 148, or may instead cooperate with blade arm 156, to maintain assembly 110 in its initial position. As another non-limiting example, spring 146 may engage with pivot arm 148 or blade arm 156 in any suitable way to urge assembly 110 from its initial position to its extended position and ultimately to its fired position. As yet another non-limiting example, blade arm 156, slider 164, and pivot arm 148 may be coupled together and cooperate with housing 108 in any suitable way.

Figures 21, 22:
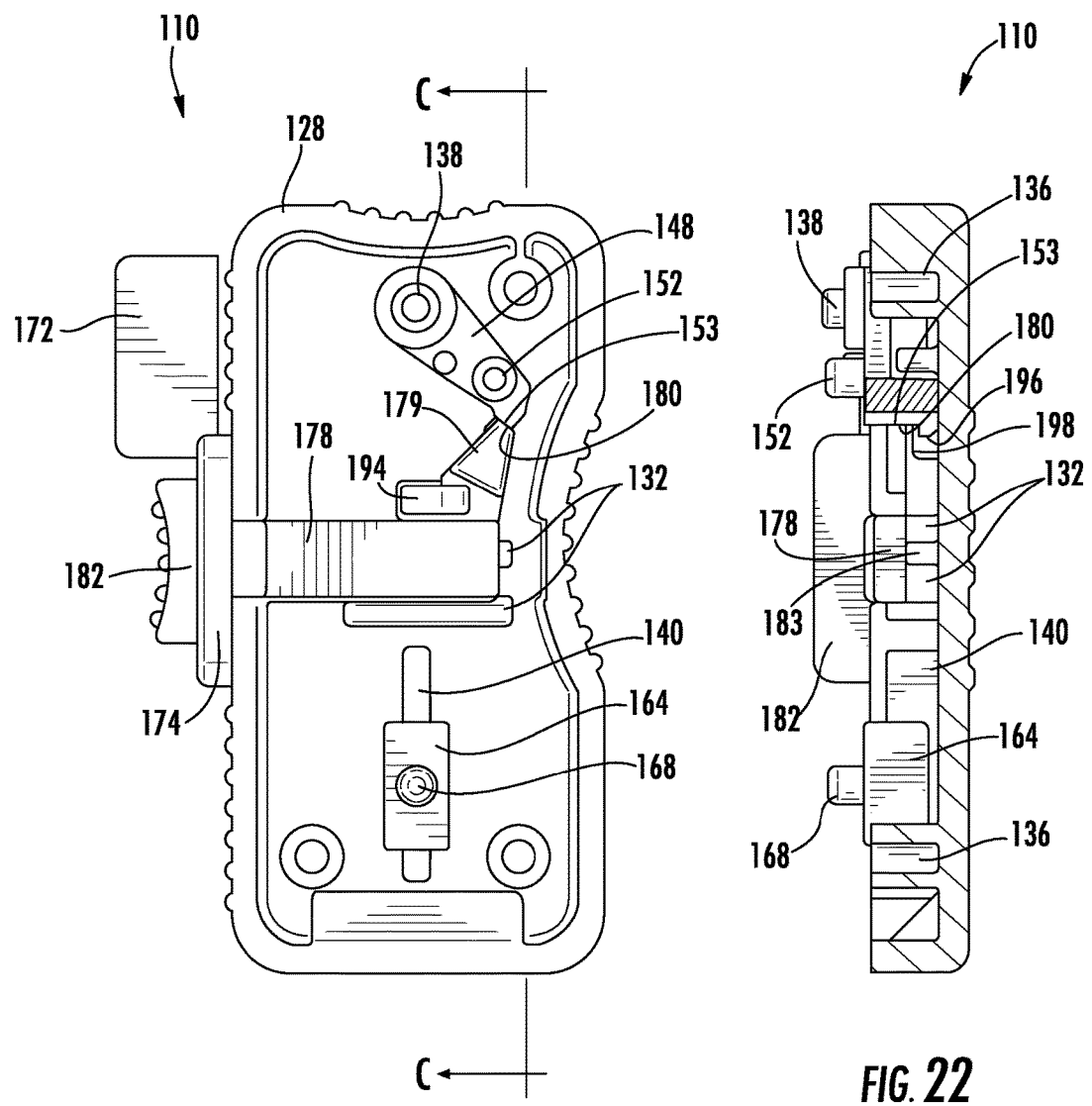
FIG. 21 is a front view of a lancet assembly according to an embodiment, shown assembled with a tab but with the front cover, the spring and the blade arm removed.
FIG. 22 is a section view of the lancet assembly of FIG. 21, taken along line C-C of FIG. 21.
Figure 23:
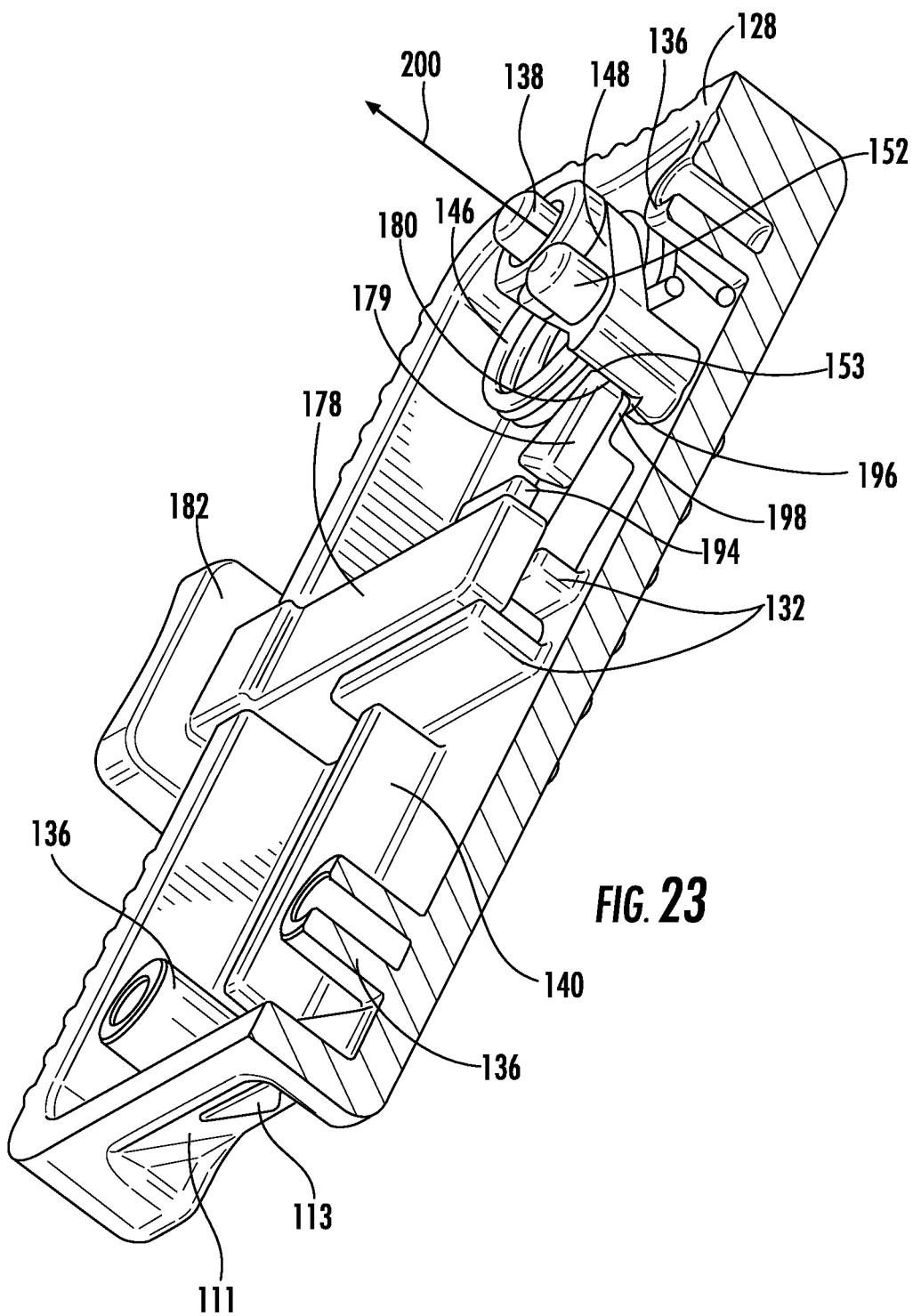
FIG. 23 is a perspective sectional view of the lancet assembly of FIG. 21, shown with the blade arm removed.
Figure 24:
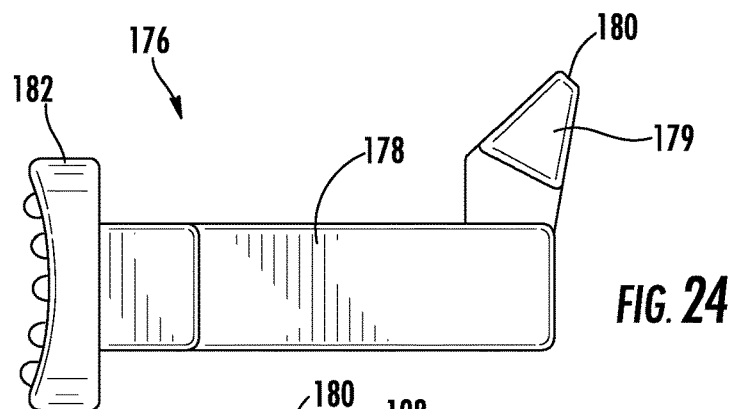
FIG. 24 is a front view of the trigger of the lancet assembly of FIG. 21, shown in isolation.
Figure 25:
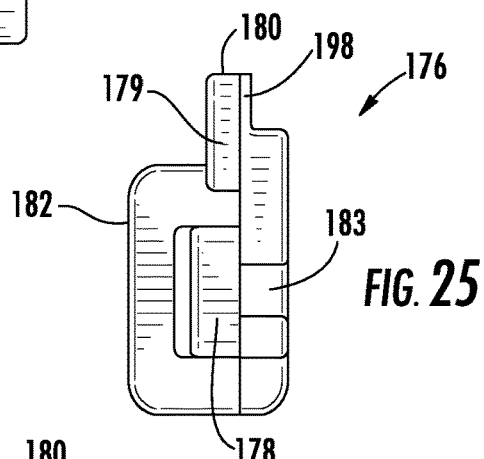
FIG. 25 is a side view of the trigger of FIG. 24.
Figure 26:
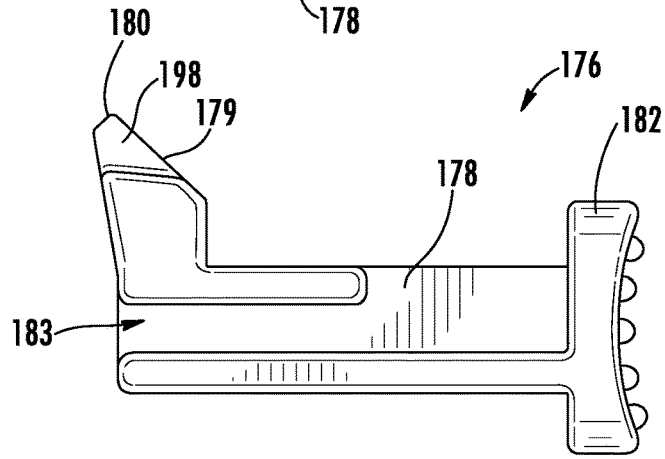
FIG. 26 is a rear view of the trigger of FIG. 24.
Figure 27:
FIG. 27 is a side view of the pivot arm of the lancet assembly of FIG. 21, shown in isolation.
Figure 28:
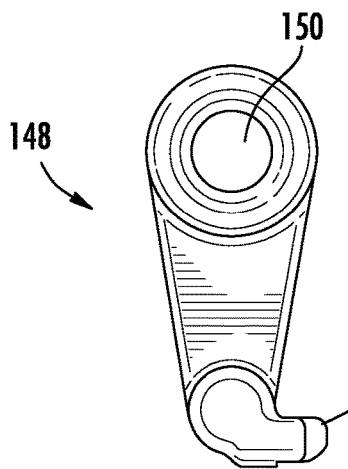
FIG. 28 is a rear view of the pivot arm of FIG. 27.
Figure 29:
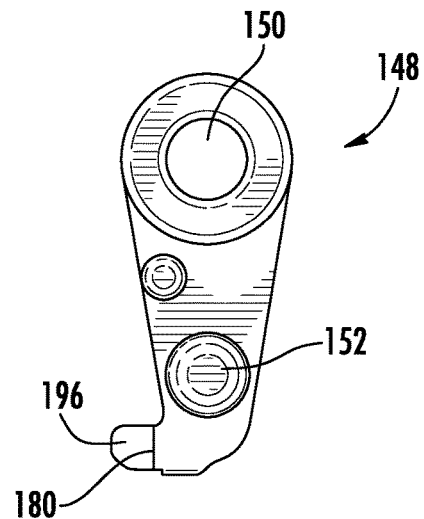
FIG. 29 is a front view of the pivot arm of FIG. 27.
Figure 30:
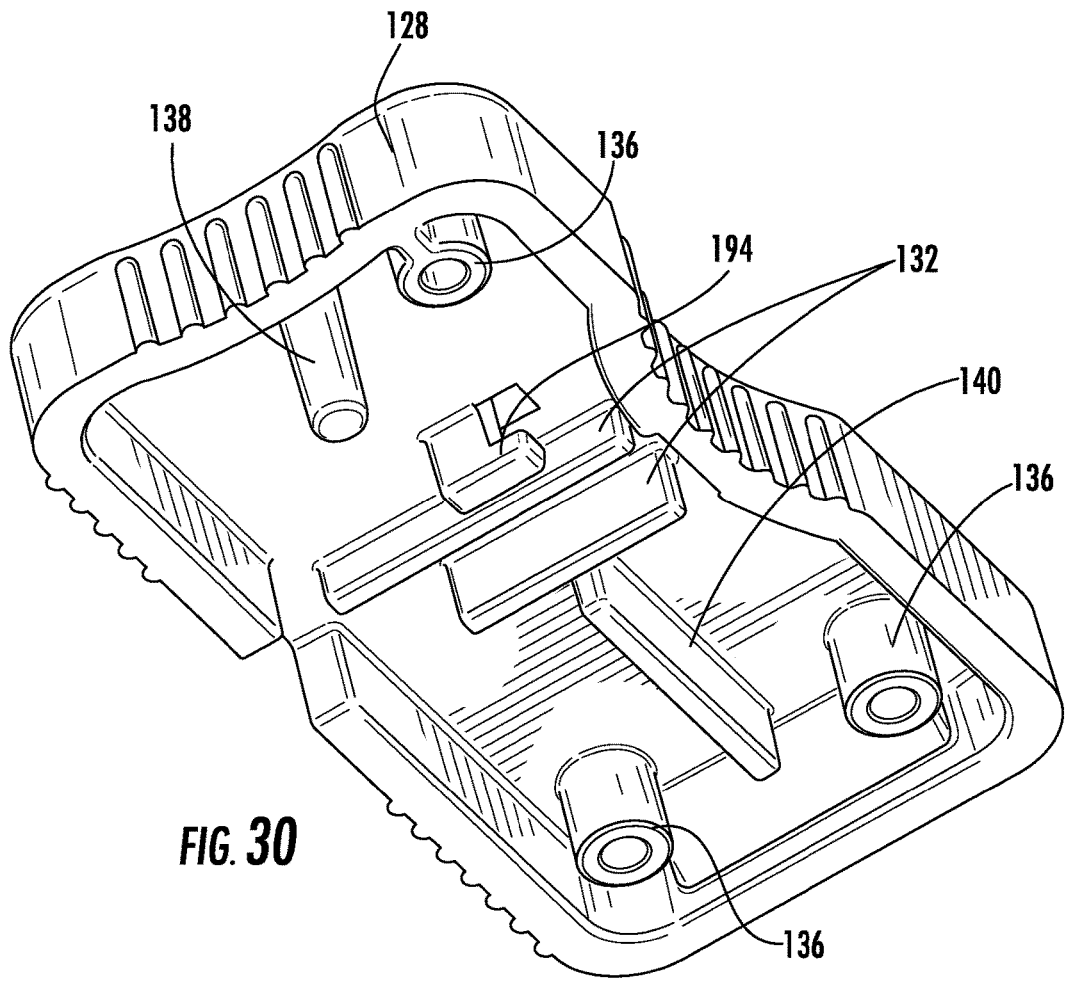
FIG. 30 is a front perspective view of the rear cover of the lancet assembly of FIG. 21, shown in isolation.

FIGS. 21-30 illustrate other non-limiting variations to assembly 110. For example, assembly 110 may include one or more latches that help resist the forces exerted by spring 146 on pivot arm 148 when the assembly 110 is in the initial position and spring 146 is in the deformed state, which helps keep assembly 110 assembled properly prior to firing. The forces of the spring can be resisted in any suitable way. As illustrated, rear cover 128 includes a latch 194, pivot arm 148 includes a latch 196, and trigger 176 includes a latch 198. These latches are configured to counteract the various forces of spring 146 and keep assembly 110 assembled throughout operation. Specifically, latch 194 on rear cover 128 exerts a force on trigger 176 that helps trigger body 178 maintain its position within housing 108. Moreover, latch 198 of trigger 176 engages latch 196 of pivot arm 148 to help oppose forces 200 (FIG. 23) exerted on pivot arm 148 by the tensioned spring 146. FIG. 22 is a cross-sectional view showing how latches 198 and 196 cooperate with one another. Because latches 194, 196, and 198 oppose the forces of spring 146 and help keep assembly 110 together in the initial position, trigger 176 need not include projections 184, as shown in FIGS. 21 and 23-26. As illustrated in FIG. 21, rear cover 128 may only include three posts 136 (instead of four as illustrated in FIGS. 18-20), thus leaving more space for the spring 146.

In some cases, pivot arm 148 includes a post or other protrusion 151 that acts as a keying feature to ensure that blade arm 156 can only be assembled in one orientation. Similarly, if desired, the leading edge 157 of blade arm 156 is configured in conjunction with post 151 so that blade arm 156 can only be assembled in one orientation onto pivot arm 148 (see FIG. 19).

The disclosed lancet assemblies are easy-to-operate and are designed to maintain the sterility and safety of the assemblies. Moreover, the trigger mechanism is designed to move in a generally X direction such that the housing of the assembly, including the surface that contacts the puncture site and from which the puncturing instrument extends, is stationary relative to the puncture site during the firing sequence. This decreases the tolerance of the assembly and allows the assembly to create incisions of reliable dimensions (including depth and width) as intended. Providing an assembly whose housing does not move relative to the incision site is beneficial because the depth and width of an incision are directly affected by the distance of the assembly from the incision site. Specifically, the locational tolerance relative to the incision site is determined by the location of the assembly when the puncturing instrument exits the assembly. Thus, when the housing (including the surface of the housing that contacts the puncture site and from which the puncturing instrument extends) moves relative to the incision site during operation, the locational tolerance of the assembly increases and the reliability of the depth and width of the incision from assembly to assembly decreases. Designing the assembly so that the housing, including the surface of the assembly housing that contacts the puncture site, does not move relative to the puncture site during firing of the assembly decreases the tolerance of the assembly and allows the designed assembly to create incisions of reliable dimensions from assembly to assembly.

Moreover, the tolerance of the disclosed assembly is further reduced by minimizing rotation and movement between the various components of the assembly. For instance, pivot arms 48 and 148 are only permitted to rotate about posts 36 and 136 and cannot translate up or down with respect to posts. This further minimizes the tolerance of the assembly, producing incisions with more reliable dimensions (i.e., depth and width).

Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A lancet assembly configured to move from an initial position to an extended position to a fired position, the lancet assembly comprising:
    (a) a housing comprising an aperture and a rail disposed in the housing;
    (b) a trigger comprising a body that at least partially extends into the housing;
    (c) a spring having a tensioned state and an expended state;
    (d) a pivot arm configured to rotate about a pivot point;
    (e) a blade arm comprising a first end, a second end opposite the first end, and a puncturing instrument, wherein the first end of the blade arm is coupled with the pivot arm and wherein the puncturing instrument is housed within the housing when the assembly is in the initial position; and
    (f) a slider coupled with the second end of the blade arm, wherein the slider is linearly slidable along the rail in a first direction and a second direction opposite the first direction, wherein movement of the slider positions the blade arm relative to the rail,
    wherein the trigger is translatable in a third direction within the housing, wherein the third direction is substantially perpendicular to the first direction and the second direction,
    wherein the assembly is configured such that activation of the trigger releases the spring from its tensioned state and:
        moves the assembly from the initial position to the extended position, during which the blade arm translates longitudinally in the first direction and rotates about the pivot point, causing the puncturing instrument to extend through the aperture and exit the housing;

moves the assembly from the extended position to the fired position, during which the blade arm translates longitudinally in the second direction opposite and rotates about the pivot point, causing the puncturing instrument to retract through the aperture into the housing and wherein movement of the assembly from the initial position to the extended position and from the extended position to the fired position does not require a corresponding longitudinal movement of the aperture.

2. The lancet assembly of claim 1, wherein the puncturing instrument is monolithically formed with the blade arm.

3. The lancet assembly of claim 1, wherein the puncturing instrument is a separate component from the blade arm.

4. The lancet assembly of claim 1, wherein the body of the trigger comprises a detent that cooperates with the blade arm or the pivot arm to maintain the spring in its tensioned state when the assembly is in the initial position.

5. The lancet assembly of claim 1, wherein the body of the trigger comprises an extension with an abutting surface configured to abut an abutting surface of the pivot arm to maintain the spring in the tensioned state when the assembly is in the initial position.

6. The lancet assembly of claim 1, further comprising at least one latch configured to oppose forces exerted by the spring in its tensioned state.

7. The lancet assembly of claim 6, wherein the at least one latch comprises:
   a first latch disposed on the housing that cooperates with the trigger;
   a second latch disposed on the pivot arm; and
   a third latch disposed on the trigger and configured to cooperate with the second latch when the assembly is in the initial position.

8. The lancet assembly of claim 1, further comprising a plurality of gripping features.

9. The lancet assembly of claim 1, wherein, when the assembly is in the initial position, the spring is in its tensioned state and is wedged between a post of the housing and a portion of the pivot arm.

10. The lancet assembly of claim 1, wherein, upon activation of the trigger, the body of the trigger is configured to translate laterally in the third direction within the housing to release the spring from its tensioned state and move the assembly from its initial position toward its extended position.

11. A lancet assembly comprising:
(a) a housing comprising an aperture and a rail disposed in the housing;
(b) a blade arm comprising a first end and a second end opposite the first end, wherein a puncturing instrument extends from the second end;
(c) a spring configured to move from a deformed state to an expended state;
(d) a pivot arm coupled with the first end of the blade arm, wherein the pivot arm is configured to rotate within the housing about a pivot point as the spring moves from the deformed state to the expended state;
(e) a slider coupled with the second end of the blade arm, wherein, as the spring moves from the deformed state to the expended state, the slider is configured to translate linearly along the rail within the housing in a first direction and a second direction opposite the first direction to extend the puncturing instrument through the aperture and out of the housing and to retract the puncturing instrument through the aperture and into the housing; and
(f) a trigger configured to cause the spring to move from the deformed state to the expended state without requiring a corresponding longitudinal movement of the aperture, wherein the trigger is translatable in a third direction within the housing, wherein the third direction is substantially perpendicular to the first direction and the second direction.

12. The lancet assembly of claim 11, wherein the housing comprises a plurality of gripping features.

13. The lancet assembly of claim 11, wherein the trigger cooperates with the pivot arm or the blade arm to maintain the spring in its deformed state.

14. The lancet assembly of claim 13, wherein the trigger comprises a detent that receives a post of the blade arm to maintain the spring in its deformed state.

15. The lancet assembly of claim 13, wherein the trigger comprises an abutting surface that abuts a corresponding abutting surface of the pivot arm to maintain the spring in its deformed state.

16. The lancet assembly of claim 11, further comprising at least one latch to oppose forces exerted by the spring in its deformed state.

17. The lancet assembly of claim 16, wherein the at least one latch comprises:
   a first latch disposed on the housing that cooperates with the trigger;
   a second latch disposed on the pivot arm; and
   a third latch disposed on the trigger and configured to cooperate with the second latch when the spring is in the deformed state.

* * * * *